United States Patent [19]

Curtis et al.

[11] 4,393,201

[45] Jul. 12, 1983

[54] DNA WHICH CODES FOR GLYCOPROTEIN OF ERA-STRAIN RABIES VIRUS

[75] Inventors: Peter J. Curtis, Berwyn; William H. Wunner, Devon, both of Pa.

[73] Assignee: The Wistar Institute, Philadelphia, Pa.

[21] Appl. No.: 318,315

[22] Filed: Nov. 4, 1981

[51] Int. Cl.³ .................... C07H 21/04; A61K 39/205
[52] U.S. Cl. ........................................ 536/27; 536/28; 536/29; 424/88; 424/89
[58] Field of Search .................................. 536/27–29; 435/172

[56] References Cited

PUBLICATIONS

Flamand, et al., "Use of Hybridoma Monoclonal Antibodies in the Detection of Antigenic Differences Between Rabies and Rabies-Related Virus Proteins, II. The Glycoprotein," J.gen. Virol., 48, 105-109, (1980).
Curtis, et al., "Cloning of Full Length cDNA from the Rabies Virus Glycoprotein Gene," The Replication of Negative Strand Viruses, Elsevier North Holland, Inc. (New York, Sep. 9, 1981), pp. 721-725.
Anilionis, et al., "Structure of the Glycoprotein Gene in Rabies Virus," Nature, 294, 275-278, (Nov. 19, 1981).
Villa-Komaroff, et al., "A Bacterial Clone Synthesizing Proinsulin," Proc. Natl. Acad. Sci, USA., 75, 3727-3731 (1978).
Maxam, et al., "Sequencing End-Labeled DNA With Base-Specific Chemical Cleavages," Meth. Enzym. 65, 499-560 (1980).
Garoff, et al., "Nucleotide Sequence of cDNA Coding for Semliki Forest Virus Membrane Glycoproteins" Nature, 288, 236-241 (1980).
Rose, "Complete Intergenic and Flanking Gene Sequences from the Genome of Vesicular Stomatitis Virus," Cell, 19, 415-421 (1980).
Rose, et al., "Vesicular Stomatitis Virus Glycoprotein is Anchored in the Viral Membrane by a Hydrophobic Domain Near the COOH Terminus," Proc. Natl. Acad. Sci. USA., 77, 3884-3888 (1980).
Wiktor, et al., "Monoclonal Antibodies Against Rabies Virus Produced by Somatic Cell Hybridization: Detection of Antigenic Variants," Proc. Natl. Acad. Sci. USA, 75, 3938-3942 (1978).

Primary Examiner—Blondel Hazel
Attorney, Agent, or Firm—Schuyler, Banner, Birch, McKie & Beckett

[57] ABSTRACT

The present invention provides a cDNA which carries the code for the glycoprotein of the ERA-strain rabies virus.

1 Claim, 5 Drawing Figures

```
AGGAAAG ATG GTT CCT CAG GCT CTC CTG TTT GTA CCC CTT CTG GTT TTT
        met val pro gln ala leu leu phe val pro leu leu val phe CCA TTG TGT TTT GGG AAA TTC CCT ATT TAC ACG ATA CTA GAC
pro leu cys phe gly lys phe pro ile tyr thr ile leu asp
                    (1)

AAG CTT GGT CCC TGG AGC CCG ATT GAC ATA CAT CAC CTC AGC
lys leu gly pro trp ser pro ile asp ile his his leu ser
(10)                                      (20)

TGC CCA AAC AAT TTG GTA GTG GAG GAC GAA GGA TGC ACC AAC
cys pro asn asn leu val val glu asp glu gly cys thr asn
                        (30)

CTG TCA GGG TTC TCC TAC ATG GAA CTT AAA GTT GGA TAC ATC
leu ser gly phe ser tyr met glu leu lys val gly tyr ile
        (40)                                      (50)

TTA GCC ATA AAA ATG AAC GGG TTC ACT TGC ACA GGC GTT GTG
leu ala ile lys met asn gly phe thr cys thr gly val val
                              (60)

ACG GAG GCT GAA ACC TAC ACT AAC TTC GTT GGT TAT GTC ACA
thr glu ala glu thr tyr thr asn phe val gly tyr val thr
                  (70)

ACC ACG TTC AAA AGA AAG CAT TTC CGC CCA ACA CCA GAT GCA
thr thr phe lys arg lys his phe arg pro thr pro asp ala
(80)                                  (90)

TGT AGA GCC GCG TAC AAC TGG AAG ATG GCC GGT GAC CCC AGA
cys arg ala ala tyr asn trp lys met ala gly asp pro arg
                          (100)

TAT GAA GAG TCT CTA CAC AAT CCG TAC CCT GAC TAC CGC TGG
tyr glu glu ser leu his asn pro tyr pro asp tyr arg trp
          (110)                                  (120)

CTT CGA ACT GTA AAA ACC ACC AAG GAG TCT CTC GTT ATC ATA
leu arg thr val lys thr thr lys glu ser leu val ile ile
                                  (130)

TCT CCA AGT GTA GCA GAT TTG GAC CCA TAT GAC AGA TCC CTT
ser pro ser val ala asp leu asp pro tyr asp arg ser leu
                    (140)

CAC TCG AGG GTC TTC CCT AGC GGG AAG TGC TCA GGA GTA GCG
his ser arg val phe pro ser gly lys cys ser gly val ala
(150)                                      (160)
```

FIG. 3A  RABIES GLYCOPROTEIN cDNA NUCLEOTIDE AND
POLYPEPTIDE SEQUENCES

```
GTG TCT TCT ACC TAC TGC TCC ACT AAC CAC GAT TAC ACC ATT
val ser ser thr tyr cys ser thr asn his asp tyr thr ile
                            (170)

TGG ATG CCC GAG AAT CCG AGA CTA GGG ATG TCT TGT GAC ATT
trp met pro glu asn pro arg leu gly met ser cys asp ile
        (180)                                    (190)

TTT ACC AAT AGT AGA GGG AAG AGA GCA TCC AAA GGG AGT GAG
phe thr asn ser arg gly lys arg ala ser lys gly ser glu
                        (200)

ACT TGC GGC TTT GTA GAT GAA AGA GGC CTA TAT AAG TCT TTA
thr cys gly phe val asp glu arg gly leu tyr lys ser leu
                (210)

AAA GGA GCA TGC AAA CTC AAG TTA TGT GGA GTT CTA GGA CTT
lys gly ala cys lys leu lys leu cys gly val leu gly leu
(220)                                    (230)

AGA CTT ATG GAT GGA ACA TGG GTC GCG ATG CAA ACA TCA AAT
arg leu met asp gly thr trp val ala met gln thr ser asn
                    (240)

GAA ACC AAA TGG TGC CCT CCC GAT CAG TTG GTG AAC CTG CAC
glu thr lys trp cys pro pro asp gln leu val asn leu his
        (250)                                (260)

GAC TTT CGC TCA GAC GAA ATT GAG CAC CTT GTT GTA GAG GAG
asp phe arg ser asp glu ile glu his leu val val glu glu
                            (270)

TTG GTC AGG AAG AGA GAG GAG TGT CTG GAT GCA CTA GAG TCC
leu val arg lys arg glu glu cys leu asp ala leu glu ser
                (280)

ATC ATG ACA ACC AAG TCA GTG AGT TTC AGA CGT CTC AGT CAT
ile met thr thr lys ser val ser phe arg arg leu ser his
(290)                                        (300)

TTA AGA AAA CTT GTC CCT GGG TTT GGA AAA GCA TAT ACC ATA
leu arg lys leu val pro gly phe gly lys ala tyr thr ile
                        (310)

TTC AAC AAG ACC TTG ATG GAA GCC GAT GCT CAC TAC AAG TCA
phe asn lys thr leu met glu ala asp ala his tyr lys ser
        (320)                                    (330)

GTC AGA ACT TGG AAT GAG ATC CTC CCT TCA AAA GGG TGT TTA
val arg thr trp asn glu ile leu pro ser lys gly cys leu
                            (340)

AGA GTT GGG GGG AGG TGT CAT CCT CAT GTG AAC GGG GTG TTT
arg val gly gly arg cys his pro his val asn gly val phe
                (350)
```

FIG. 3B

```
TTC AAT GGT ATA ATA TTA GGA CCT GAC GGC AAT GTC TTA ATC
phe asn gly ile ile leu gly pro asp gly asn val leu ile
(360)                                        (370)

CCA GAG ATG CAA TCA TCC CTC CTC CAG CAA CAT ATG GAG TTG
pro glu met gln ser ser leu leu gln gln his met glu leu
                            (380)

TTG GAA TCC TCG GTT ATC CCC CTT GTG CAC CCC CTG GCA GAC
leu glu ser ser val ile pro leu val his pro leu ala asp
        (390)                                    (400)

CCG TCT ACC GTT TTC AAG GAC GGT GAC GAG GCT GAG GAT TTT
pro ser thr val phe lys asp gly asp glu ala glu asp phe
                                (410)

GTT GAA GTT CAC CTT CCC GAT GTG CAC AAT CAG GTC TCA GGA
val glu val his leu pro asp val his asn gln val ser gly
                (420)

GTT GAC TTG GGT CTC CCG AAC TGG GGG AAG TAT GTA TTA CTG
val asp leu gly leu pro asn trp gly lys tyr val leu leu
(430)                                        (440)

AGT GCA GGG GCC CTG ACT GCC TTG ATG TTG ATA ATT TTC CTG
ser ala gly ala leu thr ala leu met leu ile ile phe leu
                    (450)

ATG ACA TGT TGT AGA AGA GTC AAT CGA TCA GAA CCT ACG CAA
met thr cys cys arg arg val asn arg ser glu pro thr gln
        (460)                                    (470)

CAC AAT CTC AGA GGG ACA GGG AGG GAG GTG TCA GTC ACT CCC
his asn leu arg gly thr gly arg glu val ser val thr pro
                                (480)

CAA AGC GGG AAG ATC ATA TCT TCA TGG GAA TCA CAC AAG AGT
gln ser gly lys ile ile ser ser trp glu ser his lys ser
                (490)

GGG GGT GAG ACC AGA CTG [TGA] GGACTGGCCGTCCTTTCAACGATCC
gly gly glu thr arg leu
(500)

AAGTCCTGAAGATCACCTCCCCTTGGGGGGTTCTTTTTAAAAA
```

FIG. 3C

DNA WHICH CODES FOR GLYCOPROTEIN OF ERA-STRAIN RABIES VIRUS

This work was supported by U.S. Public Health Service Research Grants AI-09706 from the National Institute of Allergy and Infectious Diseases, and RR 05540 from the Division of Research Sources. The invention described herein was also made in the course of work under a grant or award from the Department of Health and Human Services.

This invention relates to rabies virus, more particularly, the ERA-strain of rabies virus. Most particularly, this invention relates to DNA which carries the code for the glycoprotein of the ERA-strain rabies virus.

Rabies RNA virus is a rhabdovirus which has a single (non-segmented) negative-strand RNA genome which is transcribed upon infection to produce five polyadenylated complementary monocistronic mRNA species. Each of the virus-specific mRNA's representing a structural gene of the rabies virus genome (see Flamand and Delagneau, *J. Virol.* 28, 518-523 (1978)) codes for a virion structural protein which corresponds in size to the apparent coding capacity of its mRNA (see Pennica, et al., *Virology*, 103, 517-521 (1980); and Wunner, et al., *J. Virol.* 36, 133-142 (1980)). The glycoprotein RNA gene codes for a membrane-associated molecule which forms spike-like projections on the surface of mature rabies virions and is responsible for the induction and binding of virus-neutralizing antibodies to rabies virus (see Wiktor, et al., *J. Immun.* 110, 269-276 (1973); Cox, et al., *Infect. Immun.* 16, 754-759 (1977); and Dietzschold, et al., *J. gen. Virol.* 40, 131-139 (1978)).

Since the rabies glycoprotein is the primary antigen in rabies virus, it is expected that eventually, injection of the glycoprotein or segments of the glycoprotein which contain an antigen site into an animal will prove to be an effective immunological procedure, without the inherent risks associated with immunization of a patient with denatured rabies virus.

Rabies viruses isolated from different animal species in various parts of the world were in the past considered to be closely related by serological tests. However, several rabies-related viruses (see Shope, et al., *J. Virol.* 6, 690-692 (1970); and Tignor, et al., *J. gen. Virol.* 37, 595-611 (1977)), isolated mainly from bats and considered to belong to the same genus as rabies virus within the family Rhabdoviridae, have shown more distant serological relatedness to each other and to rabies viruses (Fenner, F. *Intervirology* 7, 42-43 (1976)). Recently, antigenic differences among rabies virus strains themselves have also been detected with monoclonal antibodies directed against the glycoprotein (see Wiktor and Koprowski, *Proc. Nat. Acad. Sci. U.S.A.* 75, 3938-3942 (1978); and Flamand, et al., *J. gen. Virol.* 48, 105-109 (1980)).

It is a primary object of the present invention to characterize a nucleotide structure for the glycoprotein gene in ERA-strain rabies virus.

It is an additional object of the present invention to provide a DNA which is suitable for analysis to appraise antigenic sites.

In accordance with the present invention, a DNA is provided which is a copy of the glycoprotein mRNA of ERA-strain rabies virus. This glycoprotein specific single-strand DNA contains an initiation codon (ATG) and a termination codon (TGA).

BRIEF DESCRIPTION OF THE FIGURES

FIGS. 3 (A-C) illustrates the complete cDNA nucleotide and corresponding predicted amino acid sequences of the ERA strain rabies glycoprotein.

Figure 1:
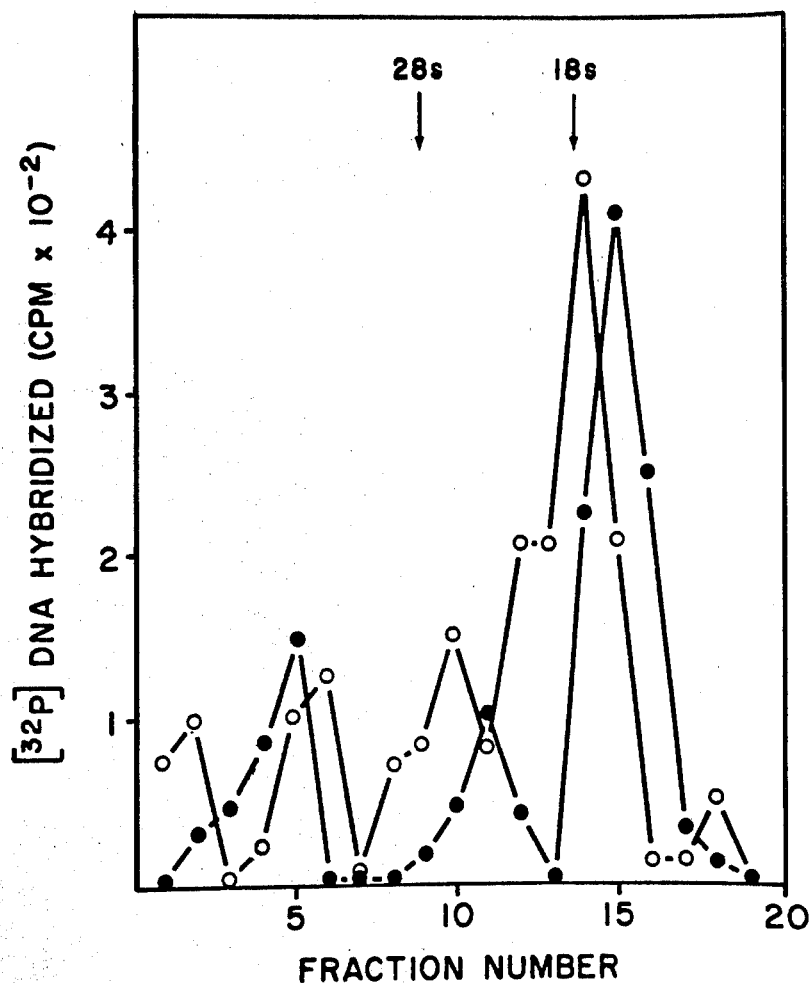
FIG. 1 illustrates the results of hybridization analysis of rabies virus surface glycoprotein polyA RNA and rabies virus nucleocapsid protein polyA RNA from rabies virus-infected cells.

According to the present invention, the entire cDNA sequence of the coding portion of the glycoprotein gene in ERA-strain rabies virus has been characterized. A cDNA copy of the glycoprotein mRNA sequence has been cloned into pBR322 plasmid in order to define the antigenic and immunogenic properties of rabies virus glycoprotein.

CLONING THE GLYCOPROTEIN mRNA SEQUENCE

To close the rabies glycoprotein mRNA, polyA RNA was isolated by oligo-dT cellulose chromatography from total RNA extracted from rabies virus-infected cells. Selection of rabies glycoprotein mRNA was achieved in size selection (sucrose gradient). The polyA RNA ranging from 15-20S was identified by the ability of the samples to direct synthesis of glycoprotein in micro-injected oocytes. Cloning of rabies virus-specific genes $M_1$, $M_2$ and L was excluded because the $M_1$ and $M_2$ proteins are synthesized by smaller mRNA's (about 12S) and the L protein is synthesized by a much larger mRNA (greater than about 28S). (See Pennica, et al., *Virology* 103, 517-521 (1980)). However, cloning of the rabies virus-specific gene for the nucleocapsid protein (NC) was not excluded, as will be further explained below.

The isolated polyA RNA was converted into double-strand complementary DNA and AMV reverse transcriptase and *E. coli* DNA polymerase I. Following digestion with $S_1$ nuclease and tailing with dCMP residues, DNA larger than 1 kilobase pairs was selected by sucrose gradient centrifugation. The selected DNA was hybridized with dG-tailed pBR322 prior to transformation of *E. coli* x1776. Tetracycline-resistant colonies were screened using $^{32}$P-labeled rabies virion RNA. Approximately one percent of the colonies responded to the probe with varying intensities. Of 100 colonies that were rescreened, 20 colonies were selected that gave the strongest signals from the probe.

Single-strand cDNA was prepared in a 400 ul-volume reaction containing 20 ug 15-20S polyA RNA from cells infected with the ERA strain of rabies virus, 50 nM (millimolar) Tris-HCl (pH 8.3), 35 mM KCl, 10 mM $MgCl_2$, 30 mM β-mercaptoethanol, 20 uCi $^3$H-dCTP (17 Ci/mmol, ICN), 0.5 mM dATP, dCTP, dGTP, dTTP, 200 ug/ml BSA and 150 units of AMV reverse transcriptase. The reaction mixture was incubated at 42° C. for 60 minutes. The cDNA (6 ug) was purified by phenol extraction and Sephadex G100 chromatography. Double-strand cDNA was synthesized in a reaction volume of 400 ul containing 25 mM Tris-HCl (pH 8.3), 70 mM KCl, 5 mM $MgCl_2$, 16 mM β-mercaptoethanol, 100 mM Hepes buffer (pH 6.9)., 50 uCi $^{32}$Pα-dCTP (400 Ci/mmol, Amersham), 0.1 mM dCTP, 0.5 mM dATP, dGTP, dTTP, and 12.5 units of *E. coli* DNA polymerase I (Boehringer Mannheim). The reaction mixture was incubated at 15° C. for 4 hours. Double-strand cDNA (5 ug) purified from the reaction as above was treated with $S_1$ nuclease (4000 units (Miles) in 0.25 M NaCl, 0.03 M sodium acetate (pH 4.5), and 1 mM $ZnCl_2$), at 37° C. for 45 minutes. The DNA (2 ug) was elongated with dCMP residues in 160 ul containing 0.1 M sodium cacodylate (pH 7.0), 2.5 mM $CoCl_2$, 150 uM dCTP, 50 ug/ml BSA and 48 units of terminal deoxynucleotide transferase (University of Zurich) by incubation at 0° C. for 30 minutes. Purified dC-tailed double-strand cDNA was fractionated according to size by sedimentation in a 5–23% sucrose gradient and centrifugation at 49,000 rpm for 5 hours at 10° C. in a SW65 rotor. DNA sedimenting between size markers of 3.2 and 1.1 kilobase pairs was pooled (0.12 ug). Double-strand cDNA tailed with dCMP residues (6 ng) was annealed with 25 ng of pBR322 which had been cleaved with Pst I and tailed with dGMP residues.

The annealed mixture yielded approximately 1000 tetracycline-resistant colonies upon transformation of *E. coli* x1776 (Villa-komaroff et al, *Proc. Nat. Acad. Sci. U.S.A.* 75, 3727–3731 (1978)). Tetracycline-resistant colonies were grown for 48 hours on agar plates before transferring them to Whatman No. 540 filters. The filters were prepared as described by Grunstein and Hogness, *Proc. Nat. Acad. Sci. U.S.A.* 72, 3961–3965 (1975), (except for an initial treatment with 0.2 N HCl for 20 minutes) and hybridized in 50% formamide (Alwine et al, *Proc. Nat. Acad. Sci. U.S.A.* 74, 5350–5354 (1977)). To prepare a probe for screening the colonies, rabies virion RNA was partially degraded by heating at 55° C. for 50 minutes in 0.05 M $Na_2CO_3$, neutralized by adjustment to 0.3 M sodium acetate (pH 5.5), and precipitated with ethanol. The partially degraded RNA (1 ug) was labeled by inclubation in 50 mM Tris-HCl (pH 8.0), 10 mM $MgCl_2$, 10 mM dithiothreitol, 50 uCi$\gamma$-$^{32}$P-ATP (about 5,000 Ci/mmol, Amersham) with 10 units of polynucleotide kinase (PL Biochemicals) at 37° C. for 60 minutes.

Plasmids from the 20 colonies selected above were checked for their size by digestion with BamH I to give linear molecules, and with Pst I to excise the cDNA insert.

Specifically, the BamH I- and Pst I- restricted plasmid DNA's containing rabies virus gene sequences were electrophoresed on 1% and 1.5% agarose gels, respectively.

About half of the plasmids contained an additional BamH I site, and these plasmids on the average contained shorter insertions than those lacking the BamH I site. This result indicated the presence of two different sequences, one for the virus glycoprotein, the other for the virus nucleocapsid protein. A plasmid was chosen from each group for further analysis: A344 which contained an insert having an estimated 1.75 kilobase pairs and lacking any additional BamH I site, and B333 which contained an insert having an estimated 1.3 kilobase pairs and having an additional BamH I site.

Two mRNA species which respectively specified the coding sequence for (a) the rabies virus surface glycoprotein and (b) the major nucleocapsid protein have been identified by translation following microinjection into *X. laevis* oocytes and radioimmunoassay to detect the polypeptide products using glycoprotein- and nucleocapsid protein-specific monoclonal antibodies (see Wunner et al., *J. Virol.* 35, 133–142 (1980)). It was determined by this assay that glycoprotein and nucleocapsid protein mRNAs sedimented at 18S and 16S, respectively.

To distinguish between the expected glycoprotein and nucleocapsid protein mRNA-specific plasmids, the inserts of A344 and B333 were isolated by Pst I digestion and electrophoresis on 1.5% agarose, gel (Tabak and Flavell, *Nucl. Acid Res.* 5, 2321–2332 (1978)).

Each insert was then labeled by nick-translation (Rigby, et al., *J. mol. Biol.* 113, 237–251 (1977)) and hybridized to individual fractions of polyA RNA derived from rabies virus-infected cells, and sedimented in a sucrose gradient.

Specifically, the labeled probes were heated at 100° C. for 5 minutes, adjusted to 50% formamide, 0.75 M NaCl, 10 mM Hepes buffer (pH 6.8), 1 mM EDTA, 1 mg/ml yeast RNA, and then heated with fractionated polyA RNA from rabies virus-infected cells in a total volume of 10 ul at 45° C. for 16 hours under paraffin oil. Hybridization was terminated by addition of cold 0.25 M NaCl, 0.03 M sodium acetate (pH 4.5), and 1 mM $ZnCl_2$. After removal of paraffin oil, $S_1$ nuclease (100 units) was added and the solution was incubated at 37° C. for 45 minutes. Acid-insoluble counts were determined by TCA precipitation.

PolyA RNA (about 130 ug) was heat-denatured at 100° C. for 1 minute and centrifuged in a 5–23% sucrose gradient at 25,000 rpm at 10° C. for 16 hours in a Beckman SW41 rotor. Each fraction (0.5 ml) from the gradient was diluted 1:60 with water and 1 ul was hybridized with labeled probe (about 3,000 cpm, specific activity $10^8$cpm/ug).

The results of this procedure are shown in FIG. 1, in which the line broken by black plotting points represents the results for the B333 plasmid, and the line broken by white plotting points represents the results for the A344 plasmid.

The insert of plasmid A344 hybridized to an mRNA sedimenting at 18S, the location of maximum mRNA activity for the synthesis of glycoprotein, while the insert of plasmid B333 hybridized to an mRNA sedimenting at 16S, the location of mRNA capable of directing the synthesis in oocytes of nucleocapsid protein. Thus, the plasmids A344 and B333 were designated as pRG (glycoprotein) and pRN (nucleocapsid protein), respectively.

Characterization of pRG

Figure 2:
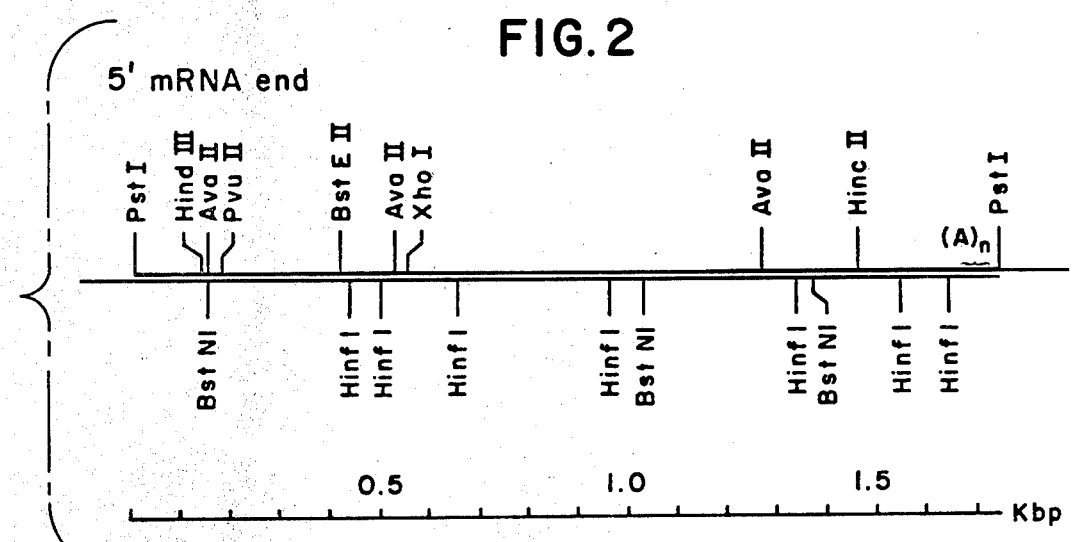
FIG. 2 illustrates the sites at which various restriction enzymes cleave rabies glycoprotein specific DNA.

The complete nucleotide sequence of the glycoprotein cDNA was determined by a technique using both 5'- and 3'- labeled restriction fragments defined by the sites indicated in FIG. 2 (Maxam and Gilbert, *Meth. Enzym.* 65, 499–560 (1980)).

More specifically, FIG. 2 shows the restriction map of the insert of pRG. At the end of the cDNA sequence corresponding to the 5'-terminus of the mRNA, an oligo-dG:dC tract of 24 residues is present while near the opposite end there is an oligo-dG:dC tract of 14 residues. These tracts were added onto the cDNA in the tailing process preparatory to annealing with pBR322. Also present at the 3' end is a sequence of polyA (designated (A)n in FIG. 2) which exists in the clone as two lengths of approximately 50 and 80 base pairs.

The complete cDNA nucleotide sequence and the deduced amino acid sequence (524 amino acids) for rabies virus glycoprotein (ERA strain) are shown in FIG. 3.

In FIG. 3 the terminology as shown in Table I is used.

TABLE I

A. Nucleotides

A = adenine   G = guanine
C = cytosine  T = thymine

B. Amino acids

| Full Name | Abbreviation | Full Name | Abbreviation |
| --- | --- | --- | --- |
| Alanine | Ala | Leucine | Leu |
| Arginine | Arg | Lysine | Lys |
| Asparagine | Asn | Methionine | Met |
| Aspartic acid | Asp | Phenylalanine | Phe |
| Cysteine | Cys | Proline | Pro |
| Glutamic acid | Glu | Serine | Ser |
| Glutamine | Gln | Threonine | Thr |
| Glycine | Gly | Tryptophan | Trp |
| Histidine | His | Tyrosine | Tyr |
| Isoleucine | Ile | Valine | Val |

In FIG. 3, boxes designate the initiation codon (ATG) and the termination codon (TGA). The initiation codon (ATG) is located at nucleotides 8-10 from the 5'-end of the clone. The other two reading frames contain numerous stop codons, such that the longest polypeptide which can be derived from them is less than 50 amino acids long.

Numbers in parenthesis in FIG. 3 designate the numerical sequence of amino acids counted from the N-terminal lysine residue of the mature glycoprotein which is located 20 amino acids from the initiation codon (ATG).

The first six amino acid residues of the mature glycoprotein, (lys - phe - pro - ile - tyr - thr -), have been identified independently by direct N-terminal amino acid sequence analysis of purified rabies virus (ERA strain) glycoprotein. The sequence of amino acids is located 20-25 residues from the initiating methionine codon in the deduced sequence.

The deduced amino acid composition of the mature rabies virus (ERA strain) glycoprotein (residues per molecule) is shown in Table II.

TABLE II

| Amino acid | Residues Per Molecule | Amino acid | Residues Per Molecule |
| --- | --- | --- | --- |
| Alanine | 20 | Leucine | 51 |
| Arginine | 28 | Lysine | 28 |
| Asparagine | 21 | Methionine | 13 |
| Aspartic acid | 25 | Phenylalanine | 18 |
| Cysteine | 16 | Proline | 28 |
| Glutamic acid | 31 | Serine | 42 |
| Glutamine | 8 | Threonine | 34 |
| Glycine | 38 | Tryptophan | 9 |
| Histidine | 18 | Tyrosine | 16 |
| Isoleucine | 22 | Valine | 39 |

The determined sequence codes for a protein of 524 amino acids including a signal peptide of 19 nonpolar acids preceding the amino-terminal lysine residue of the mature glycoprotein. The signal polypeptide is normally associated with a transmembrane protein (Lingappa et al, J. biol. Chem. 253, 8667-8670 (1978)) and is removed during maturation of the polypeptide. The amino acid residues in the structure of rabies glycoprotein cDNA shown in FIG. 3 have accordingly been numbered beginning with the N-terminal lysine of the mature glycoprotein.

An uninterrupted hydrophobic domain of 22 nonpolar amino acids bounded by the lysine residues at position 439 and two arginine residues at positions 462 and 463 near the carboxy-terminal region of the predicted polypeptide is similar to the putative transmembrane polypeptide segment of Semliki Forest Virus (SFV) glycoprotein (Garoff et al, Nature 288, 236-241 (1980)).

A relatively long sequence of 44 charged and uncharged residues extends from the putative transmembrane polypeptide domain to the carboxy-terminal leucine codon at position 505.

The deduced amino acid sequence contains four carbohydrate acceptor sites as defined by the sequence (asn-X-ser) and (asn-X-thr). Three of these sites are located on the N-terminal side of the putative transmembrane segment in the ERA-glycoprotein cDNA. Three carbohydrate chains have been found on the rabies virus glycoprotein of the ERA strain (Dietzschoid, B. J. Virol. 23, 286-293 (1977)) in agreement with the predicted number of carbohydrate attachment sites excluding the fourth carbohydrate acceptor site at positions 465-467 (which is within the putative transmembrane domain).

Completeness of Cloned mRNA Sequence

Restriction mapping established the size of the inserted cDNA of pRG as approximately 1.75 kilobase pairs (see FIG. 2).

To establish that no essential nucleotides were missing from the glycoprotein cDNA insert, a small primer fragment located close to the 5'-end of the glycoprotein sequence and bounded by the restriction sites for Pvu II and Hind III (see FIG. 2) was labeled and hybridized to 18S polyA RNA from rabies virus-infected cells. Incubation of the hybrid formed between the glycoprotein mRNA and the labeled cDNA fragment with AMV reverse transcriptase extended the primer fragment to the 5' terminus of the glycoprotein mRNA. Products of the reaction were resolved on a denaturing gel and identified by autoradiography.

The glycoprotein gene sequence was restricted with Pvu II, labeled by $\gamma$-$^{32}$P-ATP with polynucleotide kinase, and subsequently digested with Hind III. The resulting labeled fragment consisting of 36 base pairs was isolated on a 5% polyacrylamide (0.1% bis-acrylamide) gel in 50 mM Tris-borate (pH 8.3), 1 mM EDTA, eluted and dried. The $^{32}$P-labeled fragment was then denatured in 20 ul of 80% (volume/volume) formamide by heating at 100° C. for 3 minutes. A sample of 18S polyA RNA (10 ug) from rabies virus-infected cells was dried with 20 ul of solution containing 0.4 M NaCl, 20 mM Hepes buffer (pH 6.8), and 1 mM EDTA (pH 7.5). The solution of denatured $^{32}$P-labeled DNA was added to the dried RNA and incubated successively at 60° C., 58° C., 56° C., and 54° C. for 1 hour at each temperature. After annealing, the mixture was transferred into 100 ul cold 0.3 M sodium acetate (pH 5.5) and precipitated by 2.5 volumes of ethanol at −20° C. The precipitated nucleic acids were dissolved in 40 ul of 50 mM Tris-HCl (pH 8.3), 10 mM $MgCl_2$, 35 mM KCl, 30 mM $\beta$-mercaptoethanol, 0.5 mM each of the four deoxynucleoside triphosphates, 200 ug/ml BSA, 12.5 ug/ml actinomycin D and AMV reverse transcriptase (12 units), and incubated at 37° C. for 90 minutes. After precipitation from the reaction mixture with ethanol, the nucleic acids were dissolved in 4 ul 80% formamide, 50 mM Tris-borate (pH 8.3), 1 mM EDTA, 0.1% xylene cyanol FF and 0.1% bromophenol blue and heated at 90° C. for 1 minute before loading onto an 8% polyacrylamide (0.4% bis-acrylamide) gel containing 50% (weight/volume) urea, 100 mM Tris-borate (pH 8.3), and 2 mM EDTA. Labeled nucleic acids were detected by autoradiography using an intensifying screen at −70° C.

Apart from the labeled primer fragment (actual length, 36 nucleotides), the major products were approximately 40 and 165 nucleotides in length. Products having 40 nucleotides presumably arose by filling in the Hind III site recreated by the annealing of Pvu II-Hind III DNA strands, while the products having 165 nucleotides resulted from the extension of the primer which was hybridized to glycoprotein mRNA. Since the Pvu II site is located at 129 base pairs from the 5' terminus of the cloned glycoprotein sequence (excluding the small dG:dC tail of 24 base pairs), the results indicated that the cloned glycoprotein sequence is missing only about 35 nucleotides from the 5' terminus of the glycoprotein mRNA. (The inserted rabies glycoprotein cDNA sequence contains approximately 1.69 kilobase pairs). By comparison with the related vesicular stomatitis virus glycoprotein mRNA in which the 5' non-coding region contains 30 nucleotides, followed by 48 nucleotides for the signal peptide (Rose, J. K. *Cell* 19, 415–421 (1980)); and Rose et al, *Proc. Nat. Acad, Sci. U.S.A.* 77, 3884-3888 (1980)), the first methionine (see FIG. 3) is believed to be the site of initiation of glycoprotein synthesis.

The operative features of the glycoprotein cDNA are contained between the initiation codon (ATG) and the termination codon (TGA), as shown in FIG. 3. This sequence which contains the coding sequence for the glycoprotein, begins at the initiating methionine, and includes the signal sequence which consists of the first 19 codons after the initiation (ATG) codon. Hence, the fact that approximately 35 nucleotides are missing from the 5' terminus of the glycoprotein cDNA as characterized by this invention is irrelevant. The missing nucleotides are not part of the active glycoprotein coding sequence. The codons occurring before and after the initiation and termination codons, as partially disclosed in FIG. 3, are thus considered informative, but the invention particularly relates to the portion of the sequence with the initiation and termination codons as its end points.

The ERA strain of rabies virus contains a single glycoprotein form with a molecular weight of approximately 67,000, while within the cell there exists a smaller form which has a molecular weight of about 63,000 (as determined by polyacrylamide gel analysis). This smaller form of glycoprotein which lacks most of the carbohydrate of the mature form comprises at most 570 amino acids (average molecular weight 110), compatible with the deduced size of 505 residues for the mature glycoprotein.

Virus-neutralizing anti-glycoprotein monoclonal antibodies have been used to select virus variants which no longer can be neutralized by single monoclonal antibodies used for selection. Presumably, an amino acid change is responsive for the altered antibody binding sites. In order to map such changes, the cloned glycoprotein cDNA may be used to prepare primers for DNA synthesis on parent and variant virion RNA as templates in order to compare the nucleotide sequences between parent and variant viruses. Computer analysis of the sequences can be used to predict exposed antigenic regions on the virion glycoprotein.

More specifically, the cloned glycoprotein cDNA is treated by appropriate restriction enzymes and separation techniques to select for a primer sequence which is located near but not within the bounds of an antigenic site or proposed antigenic site. The resulting primer is then hybridized to glycoprotein mRNA or virion RNA from a suspected variant rabies virus strain. A cDNA for the variant in the region of the antigenic site is produced by treating the cDNA primer-hybridized mRNA or virion RNA with AMV reverse transcriptase (using the techniques earlier discussed). Differences in the product cDNA sequence as compared with the ERA-strain cDNA sequence may then be mapped by determining the new cDNA sequence using techniques already discussed above.

The cDNA of the rabies virus and variant glycoprotein mRNAs may be used to transform bacteria so that an antigenic polypeptide is produced in quantities sufficient for use in immunization. Alternatively, the antigenic polypeptide may be synthesized in vitro for use in immunization.

We claim:

1. The single strand DNA that codes for the glycoprotein of ERA-strain rabies virus beginning with an initiation codon (ATG) and ending with a termination codon (TGA), and having the nucleotide sequence as follows: ATG GTT CCT CAG GCT CTC CTG TTT GTA CCC CTT CTG GTT TTT CCA TTG TGT TTT GGG AAA TTC CCT ATT TAC ACG ATA CTA GAC AAG CTT GGT CCC TGG AGC CCG ATT GAC ATA CAT CAC CTC AGC TGC CCA AAC AAT TTG GTA GTG GAG GAC GAA GGA TGC ACC AAC CTG TCA GGG TTC TCC TAC ATG GAA CTT AAA GTT GGA TAC ATC TTA GCC ATA AAA ATG AAC GGG TTC ACT TGC ACA GGC GTT GTG ACG GAG GCT GAA ACC TAC ACT AAC TTC GTT GGT TAT GTC ACA ACC ACG TTC AAA AGA AAG CAT TTC CGC CCA ACA CCA GAT GCA TGT AGA GCC GCG TAC AAC TGG AAG ATG GCC GGT GAC CCC AGA TAT GAA GAG TCT CTA CAC AAT CCG TAC CCT GAC TAC CGC TGG CTT CGA ACT GTA AAA ACC ACC AAG GAG TCT CTC GTT ATC ATA TCT CCA AGT GTA GCA GAT TTG GAC CCA TAT GAC AGA TCC CTT CAC TCG AGG GTC TTC CCT AGC GGG AAG TGC TCA GGA GTA GCG GTG TCT TCT ACC TAC TGC TCC ACT AAC CAC GAT TAC ACC ATT TGG ATG CCC GAG AAT CCG AGA CTA GGG ATG TCT TGT GAC ATT TTT ACC AAT AGT AGA GGG AAG AGA GCA TCC AAA GGG AGT GAG ACT TGC GGC TTT GTA GAT GAA AGA GGC CTA TAT AAG TCT TTA AAA GGA GCA TGC AAA CTC AAG TTA TGT GGA GTT CTA GGA CTT AGA CTT ATG GAT GGA ACA TGG GTC GCG ATG CAA ACA TCA AAT GAA ACC AAA TGG TGC CCT CCC GAT CAG TTG GTG AAC CTG CAC GAC TTT CGC TCA GAC GAA ATT GAG CAC CTT GTT GTA GAG GAG TTG GTC AGG AAG AGA GAG GAG TGT CTG GAT GCA CTA GAG TCC ATC ATG ACA ACC AAG TCA GTG AGT TTC AGA CGT CTC AGT CAT TTA AGA AAA CTT GTC CCT GGG TTT GGA AAA GCA TAT ACC ATA TTC AAC AAG ACC TTG ATG GAA GCC GAT GCT CAC TAC AAG TCA GTC AGA ACT TGG AAT GAG ATC CTC CCT TCA AAA GGG TGT TTA AGA GTT GGG GGG AGG TGT CAT CCT CAT GTG AAC GGG GTG TTT TTC AAT GGT ATA ATA TTA GGA CCT GAC GGC AAT GTC TTA ATC CCA GAG ATG CAA TCA TCC CTC CTC CAG CAA CAT ATG GAG TTG TTG GAA TCC TCG GTT ATC CCC CTT GTG CAC CCC CTG GCA GAC CCG TCT
ACC GTT TTC AAG GAC GGT GAC GAG GCT
GAG GAT TTT GTT GAA GTT CAC CTT CCC
GAT GTG CAC AAT CAG GTC TCA GGA GTT
GAC TTG GGT CTC CCG AAC TGG GGG AAG
TAT GTA TTA CTG AGT GCA GGG GCC CTG
ACT GCC TTG ATG TTG ATA ATT TTC CTG ATG ACA TGT TGT AGA AGA GTC AAT CGA
TCA GAA CCT ACG CAA CAC AAT CTC AGA
GGG ACA GGG AGG GAG GTG TCA GTC ACT
CCC CAA AGC GGG AAG ATC ATA TCT TCA
TGG AAA TCA CAC AAG AGT GGG GGT GAG
ACC AGA CTG TGA.

\* \* \* \* \*